United States Patent [19]

Bandman et al.

[11] Patent Number: 5,759,812
[45] Date of Patent: Jun. 2, 1998

[54] HUMAN SELENIUM-BINDING PROTEIN

[75] Inventors: Olga Bandman; Phillip R. Hawkins, both of Mountain View, Calif.

[73] Assignee: Incyte Pharmaceuticals, Inc., Palo Alto, Calif.

[21] Appl. No.: 749,903

[22] Filed: Nov. 15, 1996

[51] Int. Cl.$^6$ .............. C12N 15/11; C12N 1/20; C12N 15/63; C07H 21/04
[52] U.S. Cl. .............. 435/69.2; 536/231.1; 536/24.31; 536/24.5; 536/23.5; 435/320.1; 435/252.33; 435/71.1
[58] Field of Search .............. 536/24.31, 23.1, 536/24.5, 23.5; 435/320.1, 252.33, 69.2, 71.1

[56] References Cited

PUBLICATIONS

Knekt et al., "Serum Selenium and Subsequent Risk of Cancer Among Finnish Men and Women," *Journal of National Cancer Institute*, 82(10):864–868 (1990).
Handel et al., "Inhibition of AP–1 binding and transcription by gold and selenium involving conserved cysteine residues in Jun. and Fos," *Proc. Natl. Acad. Sci. USA*, 97:4497–4501 (1995).
Bansal, "DNA sequencing of a mouse liver protein that binds selenium: implications for selenium's mechanism of action in cancer prevention," *Carcinogenesis*, 11(11):2071–2073 (1990) (GI 227630).
Bartolone et al., "Purification, Antibody Production, and Partial Amino Acid Sequence of the 58–kDa Acetaminophen–Binding Liver Proteins," *Toxicology and Applied Pharmacology*, 113:19–29 (1992).
Lanfear et al., "Different patterns of regulation of the genes encoding the closely related 56 kDA selenium–and acetaminophen–binding proteins in normal tissues and during carcinogenesis," *Carcinogenesis*, 14(3):335–340 (1993) (GI 298710).
Ishii et al., "Significant induction of a 54–kDa protein in rat liver with homologous alignment to mouse selenium binding protein by a coplanar polychlorinated biphenyl, 3, 4, 5, 3', 4'–pentachlorobiphenyl and 3–methylcholanthrene," *Toxicology Letters*, 87:1–9 (1996).
Spyrou et al., "AP–1 DNA–binding activity is inhibited by selenite and selenodiglutathione," *FEBS Letters*, 368:59–63 (1995).
Morrison et al., "Intracellular 58–kd selenoprotein levels correlate with inhibition of DNA synthesis in mammary epithelial cells," *Carcinogenesis*, 9(10):1801–1810 (1988).
Chang et al., (GI 1374792), GenBank Sequence Database (Accession 1374792), National Center for Biotechnology Information, National Library of Medicine, Bethesda, Maryland 2084.

*Primary Examiner*—Lila Feisee
*Assistant Examiner*—Geetha P. Bansal
*Attorney, Agent, or Firm*—Lucy J. Billings

[57] ABSTRACT

The present invention provides a human selenium-binding protein (HSEBP) and polynucleotides which identify and encode HSEBP. The invention also provides genetically engineered expression vectors and host cells comprising the nucleic acid sequences encoding HSEBP and a method for producing HSEBP. The invention also provides for agonists and antibodies specifically binding HSEBP, and their use in the prevention and treatment of diseases associated with expression of HSEBP. Additionally, the invention provides for the use of antisense molecules to polynucleotides encoding HSEBP for the treatment of diseases associated with the expression of HSEBP. The invention also provides diagnostic assays which utilize the polynucleotide, or fragments or the complement thereof, and antibodies specifically binding HSEBP.

9 Claims, 11 Drawing Sheets

```
5'  NNG  CGG  CCT  CTG  ACA  CCA  GCA  CAG  ACC  CGC  GAT  CAA  AGT  GTA  CCA  GTC
     X    R    P    L    T    P    A    Q    T    R    D    Q    S    V    P    V
     9              18             27             36             45             54

GGC  AGC  ATG  GCT  ACG  AAA  TGT  GGG  AAT  TGT  GGA  CCC  TAC  TCC  ACC  CCT  CTG
     G    S    M    A    T    K    C    G    N    C    G    P    Y    S    T    P    L
     63             72             81             90             99            108

GAG  GCC  ATG  AAA  GGA  CCC  AGG  GAA  GAG  ATC  GTC  TAC  CTG  CCC  TGC  ATT  TAC  CGA
     E    A    M    K    G    P    R    E    E    I    V    Y    L    P    C    I    Y    R
    117            126            135            144            153            162

AAC  ACA  GGC  ACT  GAG  GCC  CCA  GAT  TAT  CTG  GCC  ACT  GTG  GAT  GTT  GAC  CCC  AAG
     N    T    G    T    E    A    P    D    Y    L    A    T    V    D    V    D    P    K
    171            180            189            198            207            216

TCT  CCC  CAG  TAT  TGC  CAG  GTC  ATC  CAC  CGG  CTG  GCC  CGG  CTG  AAG  AAC  CTG  AAG  GAC
     S    P    Q    Y    C    Q    V    I    H    R    L    A    R    L    P    M    N    L    D
    225            234            243            252            261            270

GAG  CTG  CAT  CAC  TCA  GGA  TGG  AAC  ACC  TGC  AGC  TGC  TTC  GGT  GAT  AGC  ACC
     E    L    H    H    S    G    W    N    T    C    S    C    F    G    D    S    T
    279            288            297            306            315            324

AAG  TCG  CGC  ACC  AAG  CTG  GTG  CTG  CCC  AGT  CTC  ATC  TCC  TCT  CGC  ATC  TAT  GTG
     K    S    R    T    K    L    V    L    P    S    L    I    S    S    R    I    Y    V
    333            342            351            360            369            378
```

FIGURE 1A

```
           387           396   405           414           423           432
GTG GAC    GTG GGC TCT  GAG   CCC CGG GCC   CCA AAG CTG   CAC AAG GTC   ATT GAG CCC
 V   D      V   G   S   E      P   R   A    P   K   L     H   K   V     I   E   P 441           450   459           468           477           486
AAG GAC    ATC CAT GCC  AAG   TGC GAA CTG   GCC TTT CTC   CAC ACC AGC   CAC TGC CTG
 K   D      I   H   A   K     C   E   L     A   F   L     H   T   S     H   C   L 495           504   513           522           531           540
GCC AGC    GGG GAA GTG  ATG   ATC AGC TCC   CTG GGA GAC   GTC AAG GGC   AAT GGC AAA
 A   S      G   E   V   M     I   S   S     L   G   D     V   K   G     N   G   K 549           558   567           576           585           594
GGG GGT    TTT GTG CTG  GAT   GGG GAG ACG   TTC GAG GTG   AAG GGG ACA   TGG GAG
 G   G      F   V   L   D     G   E   T     F   E   V     K   G   T     W   E 603           612   621           630           639           648
AGA CCT    GGG GCT GCA  CCG   TTG GGC TAT   GAC TTC TGG   TAC CAG CCT   CGA CAC
 R   P      G   A   A   P     L   G   Y     D   F   W     Y   Q   P     R   H 657           666   675           684           693           702
AAT GTC    ATG ATC AGC  ACT   GAG TGG GCA   GCT CCC AAT   GTC TTA CGA   GAT GGC TTC
 N   V      M   I   S   T     E   W   A     A   P   N     V   L   R     D   G   F 711           720   729           738           747           756
AAC CCC    GCT GAT GTG  GAG   GCT GGA CTG   TAC GGG AGC   CAC TTA TAT   GTA TGG GAC
 N   P      A   D   V   E     A   G   L     Y   G   S     H   L   Y     V   W   D
```

FIGURE 1B

```
        765         774         783         792         801         810
TGG CAG CGC CAT GAG ATT GTG CAG ACC CTG TCT AAA GAT GGG CTT ATT CCC
 W   Q   R   H   E   I   V   Q   T   L   S   K   D   G   L   I   P 819         828         837         846         855         864
TTG GAG ATC CGC TTC CTG CAC AAC CCA GAC GCT GCC CAA GGC TTT GTG GGC TGC
 L   E   I   R   F   L   H   N   P   D   A   A   Q   G   F   V   G   C 873         882         891         900         909         918
GCA CTC AGC TCC ACC ATC CAG CGC TTC TAC AAG AAC GAG GGA GGT ACA TGG TCA
 A   L   S   S   T   I   Q   R   F   Y   K   N   E   G   G   T   W   S 927         936         945         954         963         972
GTG GAG AAG GTG ATC CAG GTG CCC CCC AAG AAA GTG AAG GGC TGG CTG CTG CCC
 V   E   K   V   I   Q   V   P   P   K   K   V   K   G   W   L   L   P 981         990         999         1008        1017        1026
GAA ATG CCA GGC CTG ATC ACC GAC ATC CTC TCC CTG CTC GAC CGC TTC CTC
 E   M   P   G   L   I   T   D   I   L   S   L   L   D   R   F   L 1035        1044        1053        1062        1071        1080
TAC TTC AGC AAC TGG CTG CAT GGG GAC CTG AGG CAG TAT GAC ATC TCT GAC CCA
 Y   F   S   N   W   L   H   G   D   L   R   Q   Y   D   I   S   D   P 1089        1098        1107        1116        1125        1134
CAG AGA CCC CGC CTC ACA GGA CAG CTC TTC CTC GGA GGC AGC ATT GTT AAG GGA
 Q   R   P   R   L   T   G   Q   L   F   L   G   G   S   I   V   K   G
```

FIGURE 1C

```
                1143            1152            1161            1170            1179            1188
        GGC CCT GTG CAA GTG CTG GAG GAC GAG GAA CTA AAG TCC CAG CCA GAG CCC CTA
         G   P   V   Q   V   L   E   D   E   E   L   K   S   Q   P   E   P   L 1197            1206            1215            1224            1233            1242
        GTG GTC AAG GGA AAA CGG GTG GCT GGA GGC CCT CAG ATG ATC CAG CTC AGC CTG
         V   V   K   G   K   R   V   A   G   G   P   Q   M   I   Q   L   S   L 1251            1260            1269            1278            1287            1296
        GAT GGG AAG CGC CTC TAC ATC ACC ACG TCG CTG TAC AGT GCC TGG GAC AAG CAG
         D   G   K   R   L   Y   I   T   T   S   L   Y   S   A   W   D   K   Q 1305            1314            1323            1332            1341            1350
        TTT TAC CCT GAT CTC ATC AGG GAA GGC TCT GTG ATG CTG CAG GTT GAT GTA GAC
         F   Y   P   D   L   I   R   E   G   S   V   M   L   Q   V   D   V   D 1359            1368            1377            1386            1395            1404
        ACA GTA AAA GGA GGG CTT AAG TTG AAC CCC AAC TTC CTG GTG GAC TTC GGG AAG
         T   V   K   G   G   L   K   L   N   P   N   F   L   V   D   F   G   K 1413            1422            1431            1440            1449            1458
        GAG CCC CTT GGC CCA GCC CTT GCC CAT GAG CTC CGC TAC CCT GGG GGC GAT TGT
         E   P   L   G   P   A   L   A   H   E   L   R   Y   P   G   G   D   C 1467            1476            1485            1494            1503            1512
        AGC TCT GAC ATC TGG ATT TGA ACT CCA CCC TCA CCC ACA CTC CCT ATT TTG
         S   S   D   I   W   I   *
```

FIGURE 1D

```
        1521      1530      1539      1548      1557      1566
GGC CCT CAC TTC CTT GGG GAC CTG GCT TCA TTC TGC TCT CTC TTG GCA CCC GAC 1575      1584      1593      1602      1611      1620
CCT TGG CAG CAT GTA CCA CAC AGC CAA GCT GAG ACT GTG GCA ATG TGT TGA GTC 1629      1638      1647      1656      1665      1674
ATA TAC ATT TAC TGA CCA CTG TTG CTT GTT GCT CAC TGT GCT TTT CCA TGA 1683      1692      1701      1710
GCT CTT GGA GGC ACC AAG AAA TAA ACT CGT AAC CCT GTC 3'
```

FIGURE 1E

| | | HSEBP |
|---|---|---|
| | | gl374792 |
| | | g227630 |
| | | g298710 |

FIGURE 2A

1   M A T K C G N C G P G Y S T P L E A M K G P R E E I V Y L P C I Y R N T G T E A   HSEBP
1   M A T K C G N C G P G Y S T P L E A M K G P R E E I V Y L P C I Y R N T G T E A   gl374792
1   M A T K C T K C G P G Y S T P L E A M K G P R E E I V Y L P C I Y R N T G T E A   g227630
1   M A T K C T K C G P S T P L E A M K G P R E E I V Y L P C I Y R N T G T E A       g298710

41  P D Y L A T V D V D P K S P Q Y C Q V I H R L P M P N L K D E L H H S G W N T C   HSEBP
41  P D Y L A T V D V D P K S P Q Y C Q V I H R L P M P N L K D E L H H S G W N T Y   gl374792
41  P D Y L A T V D V D P K S P Q Y S Q V I H R L P M P Y L K D E L H H S G W N T C   g227630
41  P D Y L A T V D V D P K S P Q Y S Q V I H R L P M P Y L K D E L H H S G W N T C   g298710

81  S S C F G D S T K S R T K L V L P S L I S S R I Y V V D V G S E P R A P K L H K   HSEBP
81  S S C F G D S T K S R N K L V L P S L I S S R I Y V V D V G S E P R A P K L H K   gl374792
81  S S C F G D S T K S R N K L I H L P G L M S S R I Y V V D V G S E P G P Q K L H K   g227630
81  S S C F G D S T K S R N K L I H L P G L M S S R I Y V V D V G S E P R A P K L H K   g298710

121 V I E P K D I H A K C E L A F L H T S H C L A S G E V M I S S L G D V K G N G K   HSEBP
121 V I E P K D I H A K C E L A C L H T S H C L A S G E V M I S S L G D V K G N G K   gl374792
121 V I E A S E H Q A K C N V S S L H T S H C L A S G E V M V S T L G D I Q G N G K   g227630
121 V I E A S E H Q A K C N V S N T H T S H C L A S G E V M V S T L G D L Q G N G K   g298710

161 G G F V L L D G E T F E V K G T W E R P G G A A P L G Y D F W Y Q P R H N V M I   HSEBP
161 G G F V L L D G E T F E V K G T W E R P G G A A P L G Y D F W Y Q P R H N V M I   gl374792
161 G S F V L L D G E T F E V K G T W E K P G G D A A P M G Y D F W Y Q P R H N V M V   g227630
161 G S F V L L D G E T F E V K G T W E K P G G A S P M G Y D F W Y Q P R H N V M V   g298710

```
201 STEWAAPNVLRDGFNPADVEAGLYGSHLYVVWDWQRHEIVQ  HSEBP
201 STEWAAPNVLRDGFNPADVEAGLYGSHLYVVWDWQRHEIVQ  g1374792
201 STEWAAPNVFKDGFNPAHVEAGLYGSRIFVWDWQRHEIIQ   g227630
201 STEWAAAPNVFKDGFNPAHVEAGLYGSRIFVWDWQRHEIIQ  g298710

241 TLSLKDGLIPLEIRFLHNPDAAQGFVGCALSSTIQRFYKN   HSEBP
241 TLSLKDGLIPLEIRFLHNPSATQGFVGCASAPNIQRFYKT   g1374792
241 TLQMTDGLIPLEIRFLHDPSATQGFVGCASAPNIQRFYKN   g227630
241 TLQMTDGLIPLEIRFLHDPSATQGFVGCALSSNIQRFYKN   g298710

281 EGGTWSVEKVIQVPPKKVKGWLLPEMPGLITDILLSLDDR   HSEBP
281 REGTWSVEKVIQVPPKKVKGWLLPGVPGLITDILLSLDDR   g1374792
281 AEGTWSVEKVIQVPSKKVKGWMLPGVPGLITDILLSLDDR   g227630
281 GEGTWSVEKVIQVPSKKVKGWMLPEMPGLITDILLSLDDR   g298710

321 FLYFSNWLHGDLRQYDISDPQRPRLTGQLFLGGSIVKGGP   HSEBP
321 FLYFSNWLHGDLRQYDISDPQRPRLTGQLFLGGSIVKGGP   g1374792
321 FLYFSNWLHGDIRQYDISNPQKPRLAGQIFLGGSIVRGGS   g227630
321 FLYFSNWLHGDIRQYDISNPQKPRLTGQIFLGGSIVRGGS   g298710

361 VQVLEDEELKSQPEPLVVKGKRVAGGPQMIQLSLDGKRLY   HSEBP
361 VQVLEDEELKSQPEPLVVKGKRVAGGPQMIQLSLDGKRLY   g1374792
361 VQVLEDQELTCQPEPLVVKGKRIPGGPQMIQLSLDGKRLY   g227630
361 VQVLEDQELTCQPEPLVVKGKRIPGGPQMIQLSLDGKRLY   g298710
```

FIGURE 2B

|     |                                                  |          |
|-----|--------------------------------------------------|----------|
| 401 | I T T S L Y S A W D K Q F Y P D L I R E G S V M L Q V D V D T V K G G L K L N P | HSEBP |
| 401 | I T T S L Y S A W E K Q F Y P D L I R E G S V M L Q V D V D T V K G G L K L N P | gI374792 |
| 401 | A T T S L Y S A W D K Q F Y P D L I R E G S M M L Q I D V D T V N G G L K L N P | g227630 |
| 401 | A T T S L Y S A W D K Q F Y P D L I R E G S V M L Q V D V D T V N G G L K L N P | g298710 |

|     |                                                  |          |
|-----|--------------------------------------------------|----------|
| 441 | N F L V D F G K E P L G P A L A H E L R Y P G G D C S S D I W I | HSEBP |
| 441 | N C L V D F G K E P L G P A L A H E L R Y P G G D C S S D I W I | gI374792 |
| 441 | N F L V D F G K L P L G P A A L A H E L R Y P G G D C S S D I W I | g227630 |
| 441 | N F L V D F G K E P L G P A L A H E L R Y P G G D C S S D I W I | g298710 |

FIGURE 2C

| Library | Lib Description | Abun | Pct Abun |
|---|---|---|---|
| COLNNOT13 | colon, ascending, 28 M | 2 | 0.0621 |
| PROSTUT01 | prostate tumor, 50 M, match to PROSNOT02 | 2 | 0.0619 |
| COLNNOT16 | colon, 62 M, match to COLNTUT03 | 2 | 0.0589 |
| COLNNOT11 | colon, 60 M | 1 | 0.0307 |
| TONGTUT01 | tongue tumor, carcinoma, 36 M | 1 | 0.0295 |
| PANCTUT01 | pancreatic tumor, 65 F, match to PANCNOT08 | 1 | 0.0257 |
| COLNTUT02 | colon tumor, 75 match to COLNNOT01 | 1 | 0.0220 |
| LUNGNOT03 | lung, 79 M, match to LUNGTUT02 | 1 | 0.0200 |
| LUNGTUT02 | lung tumor, metastasis, 79 M, match to LUNGNOT03 | 1 | 0.0188 |
| PROSTUT04 | prostate tumor, 57 M, match to PROSNOT06 | 1 | 0.0163 |
| CORPNOT02 | brain, corpus callosum, Alzheimer's, 74 M | 1 | 0.0152 |
| LUNGAST01 | lung, asthma, 17 M | 1 | 0.0150 |
| THYRNOT03 | thyroid tumor, adenoma, 28 F | 1 | 0.0138 |

FIGURE 5

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 472 amino acids
        ( B ) TYPE: amino acid
        ( C ) STRANDEDNESS: single
        ( D ) TOPOLOGY: linear ( i i ) MOLECULE TYPE: None ( v i i ) IMMEDIATE SOURCE:
        ( B ) CLONE: 989953

( x i ) SEQUENCE DESCRIPTION: SEQ ID NO:1:

```
Met Ala Thr Lys Cys Gly Asn Cys Gly Pro Gly Tyr Ser Thr Pro Leu
 1               5                  10                  15
Glu Ala Met Lys Gly Pro Arg Glu Glu Ile Val Tyr Leu Pro Cys Ile
            20                  25                  30
Tyr Arg Asn Thr Gly Thr Glu Ala Pro Asp Tyr Leu Ala Thr Val Asp
        35                  40                  45
Val Asp Pro Lys Ser Pro Gln Tyr Cys Gln Val Ile His Arg Leu Pro
    50                  55                  60
Met Pro Asn Leu Lys Asp Glu Leu His His Ser Gly Trp Asn Thr Cys
65                  70                  75                  80
Ser Ser Cys Phe Gly Asp Ser Thr Lys Ser Arg Thr Lys Leu Val Leu
                85                  90                  95
Pro Ser Leu Ile Ser Ser Arg Ile Tyr Val Val Asp Val Gly Ser Glu
            100                 105                 110
Pro Arg Ala Pro Lys Leu His Lys Val Ile Glu Pro Lys Asp Ile His
        115                 120                 125
Ala Lys Cys Glu Leu Ala Phe Leu His Thr Ser His Cys Leu Ala Ser
    130                 135                 140
Gly Glu Val Met Ile Ser Ser Leu Gly Asp Val Lys Gly Asn Gly Lys
145                 150                 155                 160
Gly Gly Phe Val Leu Leu Asp Gly Glu Thr Phe Glu Val Lys Gly Thr
                165                 170                 175
Trp Glu Arg Pro Gly Gly Ala Ala Pro Leu Gly Tyr Asp Phe Trp Tyr
            180                 185                 190
Gln Pro Arg His Asn Val Met Ile Ser Thr Glu Trp Ala Ala Pro Asn
        195                 200                 205
Val Leu Arg Asp Gly Phe Asn Pro Ala Asp Val Glu Ala Gly Leu Tyr
    210                 215                 220
Gly Ser His Leu Tyr Val Trp Asp Trp Gln Arg His Glu Ile Val Gln
225                 230                 235                 240
Thr Leu Ser Leu Lys Asp Gly Leu Ile Pro Leu Glu Ile Arg Phe Leu
                245                 250                 255
His Asn Pro Asp Ala Ala Gln Gly Phe Val Gly Cys Ala Leu Ser Ser
            260                 265                 270
Thr Ile Gln Arg Phe Tyr Lys Asn Glu Gly Gly Thr Trp Ser Val Glu
        275                 280                 285
Lys Val Ile Gln Val Pro Pro Lys Lys Val Lys Gly Trp Leu Leu Pro
    290                 295                 300
```

| Glu | Met | Pro | Gly | Leu | Ile | Thr | Asp | Ile | Leu | Leu | Ser | Leu | Asp | Asp | Arg |
| 305 | | | | | 310 | | | | | 315 | | | | | 320 |

| Phe | Leu | Tyr | Phe | Ser | Asn | Trp | Leu | His | Gly | Asp | Leu | Arg | Gln | Tyr | Asp |
| | | | | 325 | | | | | 330 | | | | | 335 | |

| Ile | Ser | Asp | Pro | Gln | Arg | Pro | Arg | Leu | Thr | Gly | Gln | Leu | Phe | Leu | Gly |
| | | | 340 | | | | | 345 | | | | | 350 | | |

| Gly | Ser | Ile | Val | Lys | Gly | Gly | Pro | Val | Gln | Val | Leu | Glu | Asp | Glu | Glu |
| | | 355 | | | | | 360 | | | | | 365 | | | |

| Leu | Lys | Ser | Gln | Pro | Glu | Pro | Leu | Val | Val | Lys | Gly | Lys | Arg | Val | Ala |
| | 370 | | | | | 375 | | | | | 380 | | | | |

| Gly | Gly | Pro | Gln | Met | Ile | Gln | Leu | Ser | Leu | Asp | Gly | Lys | Arg | Leu | Tyr |
| 385 | | | | | 390 | | | | | 395 | | | | | 400 |

| Ile | Thr | Thr | Ser | Leu | Tyr | Ser | Ala | Trp | Asp | Lys | Gln | Phe | Tyr | Pro | Asp |
| | | | | 405 | | | | | 410 | | | | | 415 | |

| Leu | Ile | Arg | Glu | Gly | Ser | Val | Met | Leu | Gln | Val | Asp | Val | Asp | Thr | Val |
| | | | 420 | | | | | 425 | | | | | 430 | | |

| Lys | Gly | Gly | Leu | Lys | Leu | Asn | Pro | Asn | Phe | Leu | Val | Asp | Phe | Gly | Lys |
| | | 435 | | | | | 440 | | | | | 445 | | | |

| Glu | Pro | Leu | Gly | Pro | Ala | Leu | Ala | His | Glu | Leu | Arg | Tyr | Pro | Gly | Gly |
| | 450 | | | | | 455 | | | | | 460 | | | | |

| Asp | Cys | Ser | Ser | Asp | Ile | Trp | Ile |
| 465 | | | | | 470 | | |

( 2 ) INFORMATION FOR SEQ ID NO:2:

( i ) SEQUENCE CHARACTERISTICS:
      ( A ) LENGTH: 1711 base pairs
      ( B ) TYPE: nucleic acid
      ( C ) STRANDEDNESS: single
      ( D ) TOPOLOGY: linear ( i i ) MOLECULE TYPE: None ( v i i ) IMMEDIATE SOURCE:
      ( B ) CLONE: 989953

( x i ) SEQUENCE DESCRIPTION: SEQ ID NO:2:

| GCGGCCTCTG | ACACCAGCAC | AGCAAACCCG | CCGGGATCAA | AGTGTACCAG | TCGGCAGCAT | 60 |
| GGCTACGAAA | TGTGGGAATT | GTGGACCCGG | CTACTCCACC | CCTCTGGAGG | CCATGAAAGG | 120 |
| ACCCAGGGAA | GAGATCGTCT | ACCTGCCCTG | CATTTACCGA | ACACAGGCA | CTGAGGCCCC | 180 |
| AGATTATCTG | GCCACTGTGG | ATGTTGACCC | CAAGTCTCCC | CAGTATTGCC | AGGTCATCCA | 240 |
| CCGGCTGCCC | ATGCCCAACC | TGAAGGACGA | GCTGCATCAC | TCAGGATGGA | ACACCTGCAG | 300 |
| CAGCTGCTTC | GGTGATAGCA | CCAAGTCGCG | CACCAAGCTG | GTGCTGCCCA | GTCTCATCTC | 360 |
| CTCTCGCATC | TATGTGGTGG | ACGTGGGCTC | TGAGCCCCGG | GCCCCAAAGC | TGCACAAGGT | 420 |
| CATTGAGCCC | AAGGACATCC | ATGCCAAGTG | CGAACTGGCC | TTTCTCCACA | CCAGCCACTG | 480 |
| CCTGGCCAGC | GGGGAAGTGA | TGATCAGCTC | CCTGGGAGAC | GTCAAGGGCA | ATGGCAAAGG | 540 |
| GGGTTTTGTG | CTGCTGGATG | GGAGACGTT | CGAGGTGAAG | GGACATGGG | AGAGACCTGG | 600 |
| GGGTGCTGCA | CCGTTGGGCT | ATGACTTCTG | GTACCAGCCT | CGACACAATG | TCATGATCAG | 660 |
| CACTGAGTGG | GCAGCTCCCA | ATGTCTTACG | AGATGGCTTC | AACCCCGCTG | ATGTGGAGGC | 720 |
| TGGACTGTAC | GGGAGCCACT | TATATGTATG | GGACTGGCAG | CGCCATGAGA | TTGTGCAGAC | 780 |
| CCTGTCTCTA | AAAGATGGGC | TTATTCCCTT | GGAGATCCGC | TTCCTGCACA | ACCCAGACGC | 840 |
| TGCCCAAGGC | TTTGTGGGCT | GCGCACTCAG | CTCCACCATC | CAGCGCTTCT | ACAAGAACGA | 900 |
| GGGAGGTACA | TGGTCAGTGG | AGAAGGTGAT | CCAGGTGCCC | CCCAAGAAAG | TGAAGGGCTG | 960 |

-continued

```
GCTGCTGCCC GAAATGCCAG GCCTGATCAC CGACATCCTG CTCTCCCTGG ACGACCGCTT    1020

CCTCTACTTC AGCAACTGGC TGCATGGGGA CCTGAGGCAG TATGACATCT CTGACCCACA    1080

GAGACCCCGC CTCACAGGAC AGCTCTTCCT CGGAGGCAGC ATTGTTAAGG GAGGCCCTGT    1140

GCAAGTGCTG GAGGACGAGG AACTAAAGTC CCAGCCAGAG CCCCTAGTGG TCAAGGGAAA    1200

ACGGGTGGCT GGAGGCCCTC AGATGATCCA GCTCAGCCTG GATGGGAAGC GCCTCTACAT    1260

CACCACGTCG CTGTACAGTG CCTGGGACAA GCAGTTTTAC CCTGATCTCA TCAGGGAAGG    1320

CTCTGTGATG CTGCAGGTTG ATGTAGACAC AGTAAAAGGA GGGCTGAAGT TGAACCCCAA    1380

CTTCCTGGTG GACTTCGGGA AGGAGCCCCT TGGCCCAGCC CTTGCCCATG AGCTCCGCTA    1440

CCCTGGGGGC GATTGTAGCT CTGACATCTG GATTGAACT CCACCCTCAT CACCCACACT    1500

CCCTATTTTG GGCCCTCACT TCCTTGGGGA CCTGGCTTCA TTCTGCTCTC TCTTGGCACC    1560

CGACCCTTGG CAGCATGTAC CACACAGCCA AGCTGAGACT GTGGCAATGT GTTGAGTCAT    1620

ATACATTTAC TGACCACTGT TGCTTGTTGC TCACTGTGCT GCTTTCCAT GAGCTCTTGG    1680

AGGCACCAAG AAATAAACTC GTAACCCTGT C                                  1711
```

( 2 ) INFORMATION FOR SEQ ID NO:3:

( i ) SEQUENCE CHARACTERISTICS:
        ( A ) LENGTH: 472 amino acids
        ( B ) TYPE: amino acid
        ( C ) STRANDEDNESS: single
        ( D ) TOPOLOGY: linear ( i i ) MOLECULE TYPE: None ( v i i ) IMMEDIATE SOURCE:
        ( A ) LIBRARY: GenBank
        ( B ) CLONE: 374792

( x i ) SEQUENCE DESCRIPTION: SEQ ID NO:3:

```
Met Ala Thr Lys Cys Gly Asn Cys Gly Pro Gly Tyr Ser Thr Pro Leu
 1               5                  10                  15

Glu Ala Met Lys Gly Pro Arg Glu Glu Ile Val Tyr Leu Pro Cys Ile
             20                  25                  30

Tyr Arg Asn Thr Gly Thr Glu Ala Pro Asp Tyr Leu Ala Thr Val Asp
         35                  40                  45

Val Asp Pro Lys Ser Pro Gln Tyr Cys Gln Val Ile His Arg Leu Pro
     50                  55                  60

Met Pro Asn Leu Lys Asp Glu Leu His His Ser Gly Trp Asn Thr Tyr
 65                  70                  75                  80

Ser Ser Cys Phe Gly Asp Ser Thr Lys Ser Arg Asn Lys Leu Val Leu
                 85                  90                  95

Pro Ser Leu Ile Ser Ser Arg Ile Tyr Val Val Asp Val Gly Ser Glu
            100                 105                 110

Pro Gly Pro Gln Lys Leu His Lys Val Ile Glu Pro Lys Asp Ile His
        115                 120                 125

Ala Lys Cys Glu Leu Ala Cys Leu His Thr Ser His Cys Leu Ala Ser
    130                 135                 140

Gly Glu Val Met Ile Ser Ser Leu Gly Asp Val Lys Gly Asn Gly Lys
145                 150                 155                 160

Gly Gly Phe Val Leu Leu Asp Gly Glu Thr Phe Glu Val Lys Gly Thr
                165                 170                 175

Trp Glu Arg Pro Gly Gly Ala Ala Pro Leu Gly Tyr Asp Phe Trp Tyr
            180                 185                 190
```

```
Gln Pro Arg His Asn Val Met Ile Ser Thr Glu Trp Ala Ala Pro Asn
        195                 200                 205

Val Leu Arg Asp Gly Phe Asn Pro Ala Asp Val Glu Ala Gly Leu Tyr
        210                 215                 220

Gly Ser His Leu Tyr Val Trp Asp Trp Gln Arg His Glu Ile Val Gln
225             230                 235                     240

Thr Leu Ser Leu Lys Asp Gly Leu Ile Pro Leu Glu Ile Arg Phe Leu
                245                 250                 255

His Asn Pro Ser Ala Thr Gln Gly Phe Val Gly Cys Ala Ser Ala Pro
            260                 265                 270

Asn Ile Gln Arg Phe Tyr Lys Thr Arg Glu Gly Thr Trp Ser Val Glu
            275                 280                 285

Lys Val Ile Gln Val Pro Pro Lys Lys Val Lys Gly Trp Leu Leu Pro
        290                 295                 300

Gly Val Pro Gly Leu Ile Thr Asp Ile Leu Leu Ser Leu Asp Asp Arg
305                 310                 315                 320

Phe Leu Tyr Phe Ser Asn Trp Leu His Gly Asp Leu Arg Gln Tyr Asp
                325                 330                 335

Ile Ser Asp Pro Gln Arg Pro Arg Leu Thr Gly Gln Leu Phe Leu Gly
            340                 345                 350

Gly Ser Ile Val Lys Gly Gly Pro Val Gln Val Leu Glu Asp Glu Glu
            355                 360                 365

Leu Lys Ser Gln Pro Glu Pro Leu Val Val Lys Gly Lys Arg Val Ala
        370                 375                 380

Gly Gly Pro Gln Met Ile Gln Leu Ser Leu Asp Gly Lys Arg Leu Tyr
385                 390                 395                 400

Ile Thr Thr Ser Leu Tyr Ser Ala Trp Glu Lys Gln Phe Tyr Pro Asp
                405                 410                 415

Leu Ile Arg Glu Gly Ser Val Met Leu Gln Val Asp Val Asp Thr Val
            420                 425                 430

Lys Gly Gly Leu Lys Leu Asn Pro Asn Cys Leu Val Asp Phe Gly Lys
        435                 440                 445

Glu Pro Leu Gly Pro Ala Leu Ala His Glu Leu Arg Tyr Pro Gly Gly
    450                 455                 460

Asp Cys Ser Ser Asp Ile Trp Ile
465             470
```

( 2 ) INFORMATION FOR SEQ ID NO:4:

( i ) SEQUENCE CHARACTERISTICS:
        ( A ) LENGTH: 472 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 227630

( x i ) SEQUENCE DESCRIPTION: SEQ ID NO:4:

```
Met Ala Thr Lys Cys Thr Lys Cys Gly Pro Gly Tyr Ser Thr Pro Leu
1               5                   10                  15

Glu Ala Met Lys Gly Pro Arg Glu Glu Ile Val Tyr Leu Pro Cys Ile
            20                  25                  30

Tyr Arg Asn Thr Gly Thr Glu Ala Pro Asp Tyr Leu Ala Thr Val Asp
        35                  40                  45
```

```
Val Asp Pro Lys Ser Pro Gln Tyr Ser Gln Val Ile His Arg Leu Pro
 50              55                  60
Met Pro Tyr Leu Lys Asp Glu Leu His His Ser Gly Trp Asn Thr Cys
 65              70                  75                      80
Ser Ser Cys Phe Gly Asp Ser Thr Lys Ser Arg Asn Lys Leu Ile Leu
                 85                  90                  95
Pro Gly Leu Ile Ser Ser Arg Ile Tyr Val Val Asp Val Gly Ser Glu
                100             105             110
Pro Arg Ala Pro Lys Leu His Lys Val Ile Glu Ala Ser Glu Ile Gln
            115             120             125
Ala Lys Cys Asn Val Ser Ser Leu His Thr Ser His Cys Leu Ala Ser
    130             135             140
Gly Glu Val Met Val Ser Thr Leu Gly Asp Ile Gln Gly Asn Gly Lys
145             150             155             160
Gly Ser Phe Val Leu Leu Asp Gly Glu Thr Phe Glu Val Lys Gly Thr
                165             170             175
Trp Glu Lys Pro Gly Asp Ala Ala Pro Met Gly Tyr Asp Phe Trp Tyr
            180             185             190
Gln Pro Arg His Asn Val Met Val Ser Thr Glu Trp Ala Ala Pro Asn
    195             200             205
Val Phe Lys Asp Gly Thr Asn Pro Ala His Val Glu Ala Gly Leu Tyr
    210             215             220
Gly Ser Arg Ile Phe Val Trp Asp Trp Gln Arg His Glu Ile Ile Gln
225             230             235             240
Thr Leu Gln Met Thr Asp Gly Leu Ile Pro Leu Glu Ile Arg Phe Leu
                245             250             255
His Asp Pro Ser Ala Thr Gln Gly Phe Val Gly Cys Ala Ser Ala Pro
            260             265             270
Asn Ile Gln Arg Phe Tyr Lys Asn Ala Glu Gly Thr Trp Ser Val Glu
            275             280             285
Lys Val Ile Gln Val Pro Ser Lys Lys Val Lys Gly Trp Met Leu Pro
    290             295             300
Gly Val Pro Gly Leu Ile Thr Asp Ile Leu Leu Ser Leu Asp Asp Arg
305             310             315             320
Phe Leu Tyr Phe Ser Asn Trp Leu His Gly Asp Ile Arg Gln Tyr Asp
                325             330             335
Ile Ser Asn Pro Gln Lys Pro Arg Leu Ala Gly Gln Ile Phe Leu Gly
            340             345             350
Gly Ser Ile Val Arg Gly Gly Ser Val Gln Val Leu Glu Asp Gln Glu
            355             360             365
Leu Thr Cys Gln Pro Glu Pro Leu Val Val Lys Gly Lys Arg Ile Pro
    370             375             380
Gly Gly Pro Gln Met Ile Gln Leu Ser Leu Asp Gly Lys Arg Leu Tyr
385             390             395             400
Ala Thr Thr Ser Leu Tyr Ser Ala Trp Asp Lys Gln Phe Tyr Pro Asp
                405             410             415
Leu Ile Arg Glu Gly Ser Met Met Leu Gln Ile Asp Val Asp Thr Val
            420             425             430
Asn Gly Gly Leu Lys Leu Asn Pro Asn Phe Leu Val Asp Phe Gly Lys
            435             440             445
Leu Pro Leu Gly Ala Ala Leu Ala His Glu Leu Arg Tyr Pro Gly Gly
    450             455             460
Asp Cys Ser Ser Asp Ile Trp Ile
465             470
```

( 2 ) INFORMATION FOR SEQ ID NO:5:

( i ) SEQUENCE CHARACTERISTICS:
        ( A ) LENGTH: 472 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 298710

( x i ) SEQUENCE DESCRIPTION: SEQ ID NO:5:

```
Met Ala Thr Lys Cys Thr Lys Cys Gly Pro Gly Pro Ser Thr Pro Leu
 1               5                  10                  15
Glu Ala Met Lys Gly Pro Arg Glu Glu Ile Val Tyr Leu Pro Cys Ile
                20                  25                  30
Tyr Arg Asn Thr Gly Thr Glu Ala Pro Asp Tyr Leu Ala Thr Val Asp
            35                  40                  45
Val Asp Pro Lys Ser Pro Gln Tyr Ser Gln Val Ile His Arg Leu Pro
        50                  55                  60
Met Pro Tyr Leu Lys Asp Glu Leu His His Ser Gly Trp Asn Thr Cys
 65                  70                  75                  80
Ser Ser Cys Phe Gly Asp Ser Thr Lys Ser Arg Asn Lys Leu Ile Leu
                85                  90                  95
Pro Gly Leu Met Ser Ser Arg Ile Tyr Val Val Asp Val Gly Ser Glu
               100                 105                 110
Pro Arg Ala Pro Lys Leu His Lys Val Ile Glu Ala Ser Glu Ile Gln
           115                 120                 125
Ala Lys Cys Asn Val Ser Asn Thr His Thr Ser His Cys Leu Ala Ser
       130                 135                 140
Gly Glu Val Met Val Ser Thr Leu Gly Asp Leu Gln Gly Asn Gly Lys
145                 150                 155                 160
Gly Ser Phe Val Leu Leu Asp Gly Glu Thr Phe Glu Val Lys Gly Thr
                165                 170                 175
Trp Glu Lys Pro Gly Gly Ala Ser Pro Met Gly Tyr Asp Phe Trp Tyr
            180                 185                 190
Gln Pro Arg His Asn Val Met Val Ser Thr Glu Trp Ala Ala Pro Asn
        195                 200                 205
Val Phe Lys Asp Gly Phe Asn Pro Ala His Val Glu Ala Gly Leu Tyr
    210                 215                 220
Gly Ser Arg Ile Phe Val Trp Asp Trp Gln Arg His Glu Ile Ile Gln
225                 230                 235                 240
Thr Leu Gln Met Thr Asp Gly Leu Ile Pro Leu Glu Ile Arg Phe Leu
                245                 250                 255
His Asp Pro Ser Ala Thr Gln Gly Phe Val Gly Cys Ala Leu Ser Ser
            260                 265                 270
Asn Ile Gln Arg Phe Tyr Lys Asn Gly Glu Gly Thr Trp Ser Val Glu
        275                 280                 285
Lys Val Ile Gln Val Pro Ser Lys Lys Val Lys Gly Trp Met Leu Pro
    290                 295                 300
Glu Met Pro Gly Leu Ile Thr Asp Ile Leu Leu Ser Leu Asp Asp Arg
305                 310                 315                 320
Phe Leu Tyr Phe Ser Asn Trp Leu His Gly Asp Ile Arg Gln Tyr Asp
                325                 330                 335
```

```
Ile  Ser  Asn  Pro  Gln  Lys  Pro  Arg  Leu  Thr  Gly  Gln  Ile  Phe  Leu  Gly
               340                      345                     350

Gly  Ser  Ile  Val  Arg  Gly  Gly  Ser  Val  Gln  Val  Leu  Glu  Asp  Gln  Glu
          355                      360                     365

Leu  Thr  Cys  Gln  Pro  Glu  Pro  Leu  Val  Val  Lys  Gly  Lys  Arg  Ile  Pro
     370                      375                     380

Gly  Gly  Pro  Gln  Met  Ile  Gln  Leu  Ser  Leu  Asp  Gly  Lys  Arg  Leu  Tyr
385                      390                     395                          400

Ala  Thr  Thr  Ser  Leu  Tyr  Ser  Ala  Trp  Asp  Lys  Gln  Phe  Tyr  Pro  Asp
                    405                      410                     415

Leu  Ile  Arg  Glu  Gly  Ser  Val  Met  Leu  Gln  Val  Asp  Val  Asp  Thr  Val
               420                      425                     430

Asn  Gly  Gly  Leu  Lys  Leu  Asn  Pro  Asn  Phe  Leu  Val  Asp  Phe  Gly  Lys
          435                      440                     445

Glu  Pro  Leu  Gly  Pro  Ala  Leu  Ala  His  Glu  Leu  Arg  Tyr  Pro  Gly  Gly
     450                      455                     460

Asp  Cys  Ser  Ser  Asp  Ile  Trp  Ile
465                      470
```

HUMAN SELENIUM-BINDING PROTEIN

FIELD OF THE INVENTION

This invention relates to nucleic acid and amino acid sequences of a novel human selenium-binding protein and to the use of these sequences in the diagnosis, prevention, and treatment of chemically-induced tissue damage, carcinogenesis, and cancer.

BACKGROUND OF THE INVENTION

The biological activity of selenium (Se) has been studied for over 40 years, but its precise function has not been fully elucidated. Originally identified as a highly toxic substance when ingested in large amounts, Se, usually in the form of disodium selenite ($Na_2SeO_3$), is now recognized as an essential trace element in eukaryotes and as a potent anti-carcinogenic agent in a variety of animal models (Medina, D. and D. G. Morrison (1988) Pathol. Immunopathol. Res. 7:187–199; Lane, H. W. et al. (1989) In Vivo 3:151–160; Ip, C. (1986) J. Am. Coll. Toxicol. 5:7–20; Medina D. (1986) J. Am. Coll. Toxicol. 5:7–20; Combs, G. F. and S. B Combs (1986) in *The Role of Selenium in Nutrition*, Academic Press, San Diego, Calif.; pp. 413–461). Dietary Se affords protection against both the initiation and promotion of carcinogensis, and there is increasing epidemiological evidence to support its anticarcinogenic role in humans (Knekt, P. et al. (1990) J. Natl. Cancer. Inst. 82:864–868).

Se-containing proteins are detected in a broad spectrum of tissues in vivo and in cell lines in vitro by labeling with trace amounts of radioactive [75]Se (see for example, Morrison, D. G. et al. (1988) Anticancer Res. 8:51–64; Pederson, N. D. et al. (1972) Bioinorg. Chem. 2:33–45; Calvin, H. I. (1978) J. Exp. Zool. 204:445–452; Motsenbocker, M. A. and A. L. Tappel (1982) Biochim. Biophys. Acta 709:160–165). Se is incorporated directly into proteins such as glutathione peroxidase, type I iodothyronine deiodinase, and selenoprotein P during translation. Incorporation of Se into these proteins is via the modified amino acid selenocysteine that is inserted into the nascent polypeptide in response to an in-frame UGA termination codon (Chambers, I. et al. (1986) EMBO J. 5:1221–1227; Takahashi, K. et al. (1990) J. Biochem. (Tokyo) 108:145–148; Berry, M. J. (1991) Nature 349:438–440; Hill, K. E. (1991) J. Biol. Chem. 266:10050–10053).

Some proteins do not contain selenocysteine but bind Se non-covalently. The precise nature of the binding site has not been established, but probably requires a pair of cysteine residues (Handel, M. L. et al. (1995) Proc. Natl. Acad. Sci. 92:4497–4501) because selenite is a potent oxidant of thiols. Additional structural elements must also play an important role in binding because only a limited number of $^{75}$Se-labeled proteins can be detected by SDS-polyacrylamide gel electrophoresis after labeling in vivo.

Several Se-binding proteins from mouse, rat, and human have been identified and characterized (Bansal M. P. et al. (1990) Carcinogenesis 11:2071–2073; Bartolone, J. B. et al. (1992) Toxicol. Appl. Pharmacol. 113:19–29; Lanfear, J. et al. (1993) Carcinogenesis 14:335–340; Handel, M. L. et al., supra; Ishii, Y. et al. (1996) Toxicol Lett. 87:1–9; Spyrou, G. (1995) FEBS Lett. 368:59–63; Chang, P. W. G. et al., unpublished). Some of them belong to a family of highly homologous cytosolic proteins with similar molecular weights (ca. 54–58 kDa) and overlapping tissue distributions in the kidney, liver, lung, gastrointestinal tract, and male and female endocrine glands.

At least two related, but separately regulated genes, for Se-binding proteins are present in the mouse (Lanfear, J. et al., supra). One of these encodes the previously described ~58-kDa acetaminophen-binding protein (58-ABP). 58-ABP is thought to be a target for arylation by the widely used analgesic acetaminophen and its metabolites following acute drug overdose. Arylation can lead to life-threatening liver necrosis and to kidney and lung damage.

Se-binding proteins have been implicated in cellular growth control and the protection from carcinogenesis and cancer. For example, Morrison, D. G. et al. (1988; Carcinogenesis 9:1801–1810) have correlated the inhibition of DNA synthesis with the level of Se bound to proteins in mouse mammary epithelial cells in culture. Higher levels of bound Se are observed in non-growing cells than in growing cells, but the level of protein is unaffected. This suggests that Se binding modifies the activity of pre-existing proteins. Ishii, Y. et al. (supra) have also demonstrated that synthesis of an Se-binding protein is induced in rats treated with a known disease-causing polychlorinated biphenyl (PCB) compound.

Although not structurally related to the 54–58-kDa family of Se-binding proteins, the Fos and Jun subunits of the AP-1 transcription factor also bind Se and are thereby unable to bind to their DNA recognition sequence. As a consequence, transcription from AP-1-dependent promoters is inhibited by the addition of selenite to the culture media, whereas transcription from AP-2-dependent promoters is unaffected (Handel, M. et al., supra; Spyrou, G. et al., supra). The inhibition of transcription may thus provide an explanation for some of selenium's observed biological activities.

The discovery of polynucleotides encoding the selenium-binding protein, and the molecules themselves, provides the means to investigate the regulation of DNA synthesis and transcription by inorganic ions. Discovery of molecules related to the selenium-binding protein satisfies a need in the art by providing new diagnostic or therapeutic compositions useful in the diagnosis, prevention, and treatment of conditions and diseases associated with the activity of selenium-binding proteins such as liver necrosis and kidney or lung damage resulting from acetaminophen toxicity, as well as liver, kidney, lung, mammary, epithelial, gastrointestinal, and endocrine cancer.

SUMMARY OF THE INVENTION

The present invention features a novel human selenium-binding protein hereinafter designated HSEBP and characterized as having chemical and structural homology to selenium-binding proteins of fetal human heart, mouse, and rat. Accordingly, the invention features a substantially purified HSEBP having the amino acid sequence, SEQ ID NO:1.

One aspect of the invention features isolated and substantially purified polynucleotides that encode HSEBP. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode HSEBP. The present invention also features antibodies which bind specifically to HSEBP, and pharmaceutical compositions comprising substantially purified HSEBP. The invention also features the use of agonists and antagonists of HSEBP.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:2) of HSEBP. The alignment was produced using MacDNASIS PRO™ software (Hitachi Software Engineering Co., Ltd., San Bruno, Calif.).

FIGS. 2A, 2B, and 2C show the amino acid sequence alignments among HSEBP (SEQ ID NO:1), human fetal heart Se-binding protein (G1374792; SEQ ID NO:3), mouse liver Se-binding protein (G227630; SEQ ID NO:4), and mouse liver acetaminophen-binding protein (G298710; SEQ ID NO:5). The alignment was produced using the multisequence alignment program of DNASTAR™ software (DNASTAR Inc, Madison Wis.).

FIG. 5 shows the northern analysis for SEQ ID NO:2. The northern analysis was produced electronically using LIFESEQ FL™ database (Incyte Pharmaceuticals, Inc., Palo Alto, Calif.).

DESCRIPTION OF THE INVENTION

Figure 3:
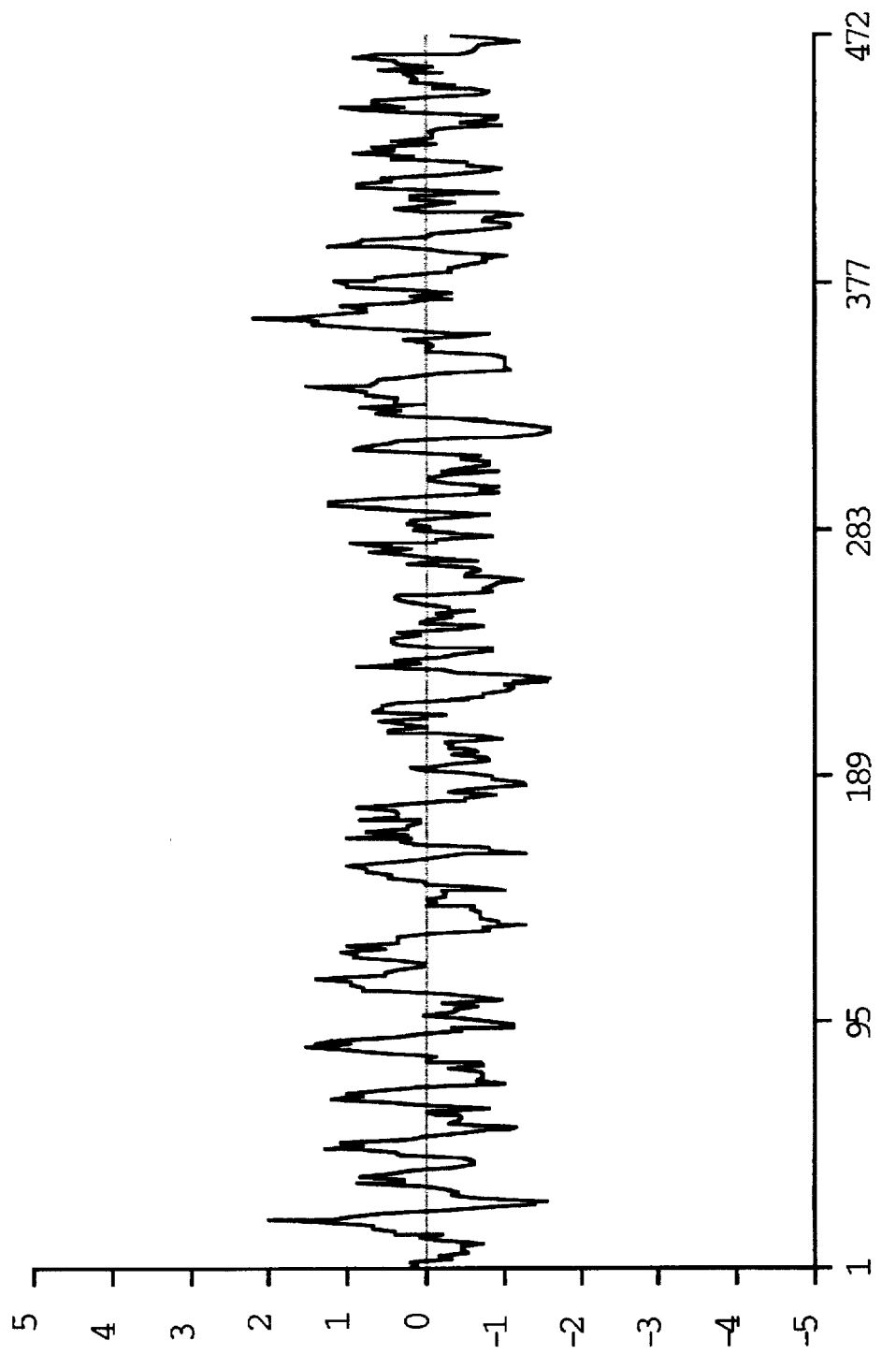
FIG. 3 shows the hydrophobicity plot (MacDNASIS PRO software) for HSEBP, SEQ ID NO:1; the positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

"Nucleic acid sequence" as used herein refers to an oligonucleotide, nucleotide, or polynucleotide, and fragments or portions thereof, and to DNA or RNA of genomic or synthetic origin which may be single- or double-stranded, and represents the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

HSEBP, as used herein, refers to the amino acid sequences of substantially purified HSEBP obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of HSEBP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic HSEBP, or any oligopeptide thereof, to induce a specific immune response in appropriate animals or cells and to bind with specific antibodies.

The term "agonist", as used herein, refers to a molecule which, when bound to HSEBP, causes a change in HSEBP which modulates the activity of HSEBP. Agonists may include proteins, nucleic acids, carbohydrates, or any other molecules which bind to HSEBP.

The terms "antagonist" or "inhibitor", as used herein, refer to a molecule which, when bound to HSEBP, modulates or blocks the biological or immunological activity of HSEBP. Antagonists and inhibitors may include proteins, nucleic acids, carbohydrates, or any other molecules which bind to HSEBP.

The term "modulate", as used herein, refers to a change or an alteration in the biological activity of HSEBP. Modulation may be an increase or a decrease in protein activity, a change in binding characteristics, or any other change in the biological, functional or immunological properties of HSEBP.

The term "mimetic", as used herein, refers to a molecule, the structure of which is developed from knowledge of the structure of HSEBP or portions thereof and, as such, is able to effect some or all of the actions of selenium-binding-like molecules.

The term "derivative", as used herein, refers to the chemical modification of a nucleic acid encoding HSEBP or the encoded HSEBP. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, the sequence "A—G—T" binds to the complementary sequence "T—C—A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm–5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human HSEBP and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding HSEBP or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding HSEBP in a sample and thereby correlates with expression of the transcript from the polynucleotide encoding the protein.

"Alterations" in the polynucleotide of SEQ ID NO:2, as used herein, comprise any alteration in the sequence of polynucleotides encoding HSEBP including deletions, insertions, and point mutations that may be detected using hybridization assays. Included within this definition is the detection of alterations to the genomic DNA sequence which encodes HSEBP (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding HSEBP (e.g., using fluorescent in situ hybridization [FISH] to metaphase chromosome spreads).

As used herein, the term "antibody" refers to intact molecules as well as fragments thereof, such as Fa, F(ab')$_2$, and Fv, which are capable of binding the epitopic determinant. Antibodies that bind HSEBP polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

The Invention

The invention is based on the discovery of a novel human selenium-binding protein (HSEBP), the polynucleotides encoding HSEBP, and the use of these compositions for the diagnosis, prevention or treatment of conditions and diseases such as liver necrosis, and kidney or lung damage resulting from chemical toxicity, as well as liver, kidney, lung, mammary, epithelial, gastrointestinal, and endocrine cancer.

Nucleic acids encoding the HSEBP of the present invention were first identified in Incyte Clone 989953 from the colon cDNA library (COLNNOT11) through a computer-generated search for amino acid sequence alignments. A consensus sequence, SEQ ID NO:2, was derived from the following overlapping and/or extended nucleic acid sequences: Incyte Clones 989953 (COLNNOT11), 609011, 1226183, and 1227155 (COLNNOT01), 1334268 (COLNNOT13),1284686 (COLNNOT16),1391936 (THYRNOT03), (COLNNOT01), 959734 (BRSTTUT03, 892480 (STOMTUT01), and 814959 (OVARTUT01).

Figure 4:
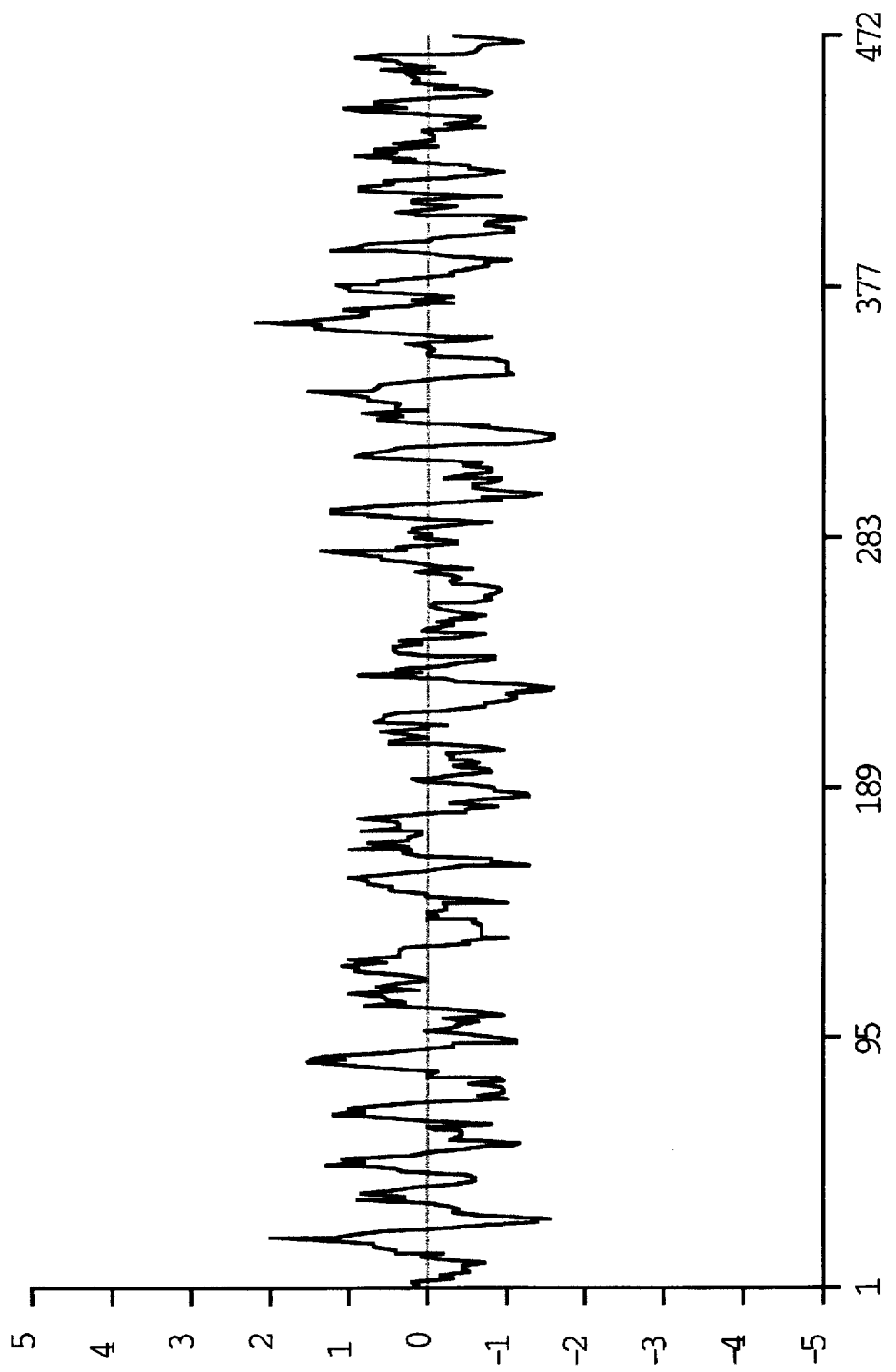
FIG. 4 shows the hydrophobicity plot for G1374792, SEQ ID NO:4.

In one embodiment, the invention encompasses the novel human selenium-binding protein, a polypeptide comprising the amino acid sequence of SEQ ID NO:1, as shown in FIGS. 1A,B,C. HSEBP is 472 amino acids in length and has no predicted transmembrane domains, potential glycosylation or phosphorylation sites. HSEBP is enriched in leucine and glycine residues which together constitute more than 20% of the total amino acid content. As shown in FIGS. 1A,B,C, there are no in-frame TGA termination codons in the nucleic acid sequence of SEQ ID NO:2 to direct the incorporation of selenocysteine into the protein of SEQ ID NO:1. HSEBP has chemical and structural homology with the human fetal heart selenium-binding protein (G1374972; SEQ ID NO:3), mouse liver selenium-binding protein (G227630; SEQ ID NO:4), and mouse liver acetaminophen-binding protein (G298710; SEQ ID NO:5). In particular, HSEBP shares 96%, 86%, and 88% identity, respectively, with each of these proteins. As illustrated by FIGS. 3 and 4, HSEBP and human fetal heart selenium-binding protein have rather similar hydrophobicity plots. Their isoelectric points, 5.91 and 6.13, respectively, are also similar. Northern analysis (FIG. 5) shows the expression of the HSEBP sequence in various libraries. Approximately 50% of these libraries are from cancerous tissues and 38% are from the gastrointestinal tract.

The invention also encompasses HSEBP variants. A preferred HSEBP variant is one having at least 80%, and more preferably 90%, amino acid sequence similarity to the HSEBP amino acid sequence (SEQ ID NO:1). A most preferred HSEBP variant is one having at least 95% amino acid sequence similarity to SEQ ID NO:1.

The invention also encompasses polynucleotides which encode HSEBP. Accordingly, any nucleic acid sequence which encodes the amino acid sequence of HSEBP can be used to generate recombinant molecules which express HSEBP. In a particular embodiment, the invention encompasses the polynucleotide comprising the nucleic acid sequence of SEQ ID NO:2 as shown in FIGS. 1A,B,C.

It will be appreciated by those skilled in the art that as a result of the degeneracy of the genetic code, a multitude of nucleotide sequences encoding HSEBP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HSEBP, and all such variations are to be considered as being specifically disclosed.

Although nucleotide sequences which encode HSEBP and its variants are preferably capable of hybridizing to the nucleotide sequence of the naturally occurring HSEBP under appropriately selected conditions of stringency, it may be advantageous to produce nucleotide sequences encoding HSEBP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HSEBP and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode HSEBP and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding HSEBP or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding HSEBP which are encompassed by the invention include deletions, insertions, or substitutions of different nucleotides resulting in a polynucleotide that encodes the same or a functionally equivalent HSEBP. The encoded protein may also contain deletions, insertions, or substitutions of amino acid residues which produce a silent change and result in a functionally equivalent HSEBP. Deliberate amino acid substitutions may be made on the basis of similarity in polarity, charge, solubility, hydrophobicity, hydrophilicity, and/or the amphipathic nature of the residues as long as the biological activity of HSEBP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; and phenylalanine and tyrosine.

Also included within the scope of the present invention are alleles of the genes encoding HSEBP. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, Sequenase® (U.S. Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding HSEBP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HSEBP, or fusion proteins or functional equivalents thereof, may be used in recombinant DNA molecules to direct expression of HSEBP in appropriate host cells. Due to the inherent degeneracy of the genetic code, other DNA sequences which encode substantially the same or a functionally equivalent amino acid sequence may be produced and these sequences may be used to clone and express HSEBP.

As will be understood by those of skill in the art, it may be advantageous to produce HSEBP-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter HSEBP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding HSEBP may be ligated to a heterologous sequence to encode a fusion protein. For example, to screen peptide libraries for inhibitors of HSEBP activity, it may be useful to encode a chimeric HSEBP protein that can be recognized by a commercially available antibody. A fusion protein may also be engineered to contain a cleavage site located between the HSEBP encoding sequence and the heterologous protein sequence, so that HSEBP may be cleaved and purified away from the heterologous moiety.

In another embodiment, sequences encoding HSEBP may be synthesized, in whole or in part, using chemical methods well known in the art (see Caruthers, M. H. et al. (1980) Nuc. Acids Res. Symp. Ser. 215–233; Horn, T. et al. (1980) Nuc. Acids Res. Symp. Ser. 225–232). Alternatively, the protein itself may be produced using chemical methods to synthesize the amino acid sequence of HSEBP, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) Proteins, Structures and Molecular Principles, WH Freeman and Co., New York, N.Y.). The composition of the synthetic peptides may be confirmed by amino acid analysis or sequencing (e.g., the Edman degradation procedure; Creighton, supra). Additionally, the amino acid sequence of HSEBP, or any part thereof, may be altered during direct synthesis and/or combined using chemical methods with sequences from other proteins, or any part thereof, to produce a variant polypeptide.

In order to express a biologically active HSEBP, the nucleotide sequences encoding HSEBP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding HSEBP and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding HSEBP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, La Jolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HSEBP, vectors based on SV40 or EBV may be used with an appropriate selectable marker.

In bacterial systems, a number of expression vectors may be selected depending upon the use intended for HSEBP. For example, when large quantities of HSEBP are needed for the induction of antibodies, vectors which direct high level expression of fusion proteins that are readily purified may be used. Such vectors include, but are not limited to, the multifunctional E. coli cloning and expression vectors such as Bluescript® (Stratagene), in which the sequence encoding HSEBP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding HSEBP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in *McGraw Hill Yearbook of Science and Technology* (1992) McGraw Hill, New York, N.Y.; pp. 191–196.

An insect system may also be used to express HSEBP. For example, in one such system, *Autographa californica* nuclear polyhedrosis virus (AcNPV) is used as a vector to express foreign genes in *Spodoptera frugiperda* cells or in Trichoplusia larvae. The sequences encoding HSEBP may be cloned into a non-essential region of the virus, such as the polyhedrin gene, and placed under control of the polyhedrin promoter. Successful insertion of HSEBP will render the polyhedrin gene inactive and produce recombinant virus lacking coat protein. The recombinant viruses may then be used to infect, for example, *S. frugiperda* cells or Trichoplusia larvae in which HSEBP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding HSEBP may be ligated into an adenovirus transcription/translation complex consisting of the late promoter and tripartite leader sequence. Insertion in a non-essential E1 or E3 region of the viral genome may be used to obtain a viable virus which is capable of expressing HSEBP in infected host cells (Logan, J. and T. Shenk (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding HSEBP. Such signals include the ATG initiation codon and adjacent sequences. In cases where sequences encoding HSEBP, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express HSEBP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al. (1981) J. Mol. Biol. 150:1–14) and als or pat, which confers resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HSEBP is inserted within a marker gene sequence, recombinant cells containing sequences encoding HSEBP can be identified by the absence of marker gene function. Alternatively, a marker gene can be placed in tandem with a sequence encoding HSEBP under the control of a single promoter. Expression of the marker gene in response to induction or selection usually indicates expression of the tandem gene as well.

Alternatively, host cells which contain the nucleic acid sequence encoding HSEBP and express HSEBP may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein.

The presence of polynucleotide sequences encoding HSEBP can be detected by DNA—DNA or DNA-RNA hybridization or amplification using probes or portions or fragments of polynucleotides encoding HSEBP. Nucleic acid amplification based assays involve the use of oligonucleotides or oligomers based on the sequences encoding HSEBP to detect transformants containing DNA or RNA encoding HSEBP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of HSEBP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HSEBP is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HSEBP include oligolabeling, nick translation, end-labeling or PCR amplification using a labeled nucleotide. Alternatively, the sequences encoding HSEBP, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding HSEBP may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode HSEBP may be designed to contain signal sequences which direct secretion of HSEBP through a prokaryotic or eukaryotic cell membrane. Other recombinant constructions may be used to join sequences encoding HSEBP to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HSEBP may be used to facilitate purification. One such expression vector provides for expression of a fusion protein containing HSEBP and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992), Prot. Exp. Purif. 3:263–281) while the enterokinase cleavage site provides a means for purifying HSEBP from the fusion protein. A discussion of vectors which contain fusion proteins is provided in Kroll, D. J. et al. (1993; DNA Cell Biol. 12:441–453).

In addition to recombinant production, fragments of HSEBP may be produced by direct peptide synthesis using solid-phase techniques (Merrifield, J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of HSEBP may be chemically synthesized separately and combined using chemical methods to produce the full length molecule.

Therapeutics

HSEBP or fragments thereof may be used for therapeutic purposes. Based on the chemical and structural homology among HSEBP (SEQ ID NO:1) and other selenium-binding proteins and northern analysis (FIG. 5) which shows that most of the libraries containing HSEBP transcripts are associated with cancer and/or the gastrointestinal and respiratory tracts, HSEBP is believed to have a role in protecting a subject from the body's response to chemical toxins and cancer.

In one embodiment, HSEBP, or a fragment or derivative thereof, may be administered to a subject to prevent or treat liver necrosis and kidney or lung damage caused by chemical agents including, but not limited to, acetaminophen and carcinogens such as PCBs. Similarly, a vector capable of expressing HSEBP may be administered to a subject to prevent or treat liver necrosis and kidney or lung damage caused by chemical agents. Once administered, HSEBP will serve as a substrate for arylation by acetaminophen and its metabolites, sparing endogenous HSEBP from modification, and thereby protecting the tissue from life-threatening damage.

Expression of HSEBP has been shown to be highly correlated with cancer (FIG. 5). Therefore, vectors containing the nucleic acid sequence encoding HSEBP may be administered to a subject to prevent or inhibit tumor growth. These vectors can be delivered into the tissue(s) of a subject that has a predisposition to cancer, or they may be administered directly into tumors or cancerous cells using technologies well known in the art. HSEBP administered by vector may serve as an intracellular reservoir of Se.

In another embodiment, HSEBP may be administered in combination therapy with other chemotherapeutic agents. Such combinations of therapeutic agents having different mechanisms of action for the treatment of cancer will have synergistic effects allowing the use of lower effective doses of each agent and lessening side effects.

In another embodiment, agonists of HSEBP may be used in those situations where such modulation is therapeutically desirable. Such agonists may be produced using methods which are generally known in the art. A particular method involves the use of purified HSEBP to screen libraries of pharmaceutical agents for those which specifically bind HSEBP.

Purified HSEBP can also be used to produce antibodies that are specific for HSEBP. The specific antibodies may be used to target or deliver a pharmaceutical agent to particular cells or tissues which express HSEBP. The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HSEBP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to HSEBP have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of HSEBP amino acids may be fused with those of another protein such as keyhole limpet hemocyanin and antibody produced against the chimeric molecule.

Monoclonal antibodies to HSEBP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce HSEBP-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for HSEBP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HSEBP and its specific antibody. A two-site, monoclonal-based immunoassay utilizing monoclonal antibodies reactive to two non-interfering HSEBP epitopes is preferred, but a competitive binding assay may also be employed (Maddox, supra).

In another embodiment of the invention, the polynucleotides encoding HSEBP, or any fragment thereof, or antisense molecules, may be used for therapeutic purposes. In one aspect, antisense to the polynucleotide encoding HSEBP may be used in situations in which it would be desirable to block the transcription of the MRNA. In particular, cells may be transformed with sequences complementary to polynucleotides encoding HSEBP. Thus, antisense molecules may be used to modulate HSEBP activity, or to achieve regulation of gene function. Such technology is now well known in the art, and sense or antisense oligomers or larger fragments, can be designed from various locations along the coding or control regions of sequences encoding HSEBP.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding HSEBP. These techniques are described both in Sambrook, J. et al. (supra) and in Ausubel et al. (supra).

Genes encoding HSEBP can be turned off by transforming a cell or tissue with expression vectors which express high levels of a polynucleotide or fragment thereof which encodes HSEBP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding HSEBP, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Future Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HSEBP.

Specific ribozyme cleavage sites within any potential RNA target are initially identified by scanning the target molecule for ribozyme cleavage sites which include the following sequences: GUN, GUN, and GUN. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HSEBP. Such DNA sequences may be incorporated into a wide variety of vectors with suitable RNA polymerase promoters such as T7 or SP6. Alternatively, these cDNA constructs that synthesize antisense RNA constitutively or inducible can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl phosphodiester linkages within the backbone of the molecule. This concept is inherent in the production of PANS and can be extended in all of these molecules by the inclusion of nontraditional bases such as inosine, queosine, and wybutosine, as well as acetyl-, methyl-, thin-, and similarly modified forms of adenine, cytidine, guanine, thymine, and uridine which are not as easily recognized by endogenous endonucleases.

Many methods for introducing vectors into cells or tissues are available and equally suitable for use in vivo in vitro, and ex vivo. For ex vivo therapy, vectors may be introduced into stem cells taken from the patient and cluneal propagated for autologous transplant back into that same patient. Delivery by transfection and by liposome injections may be achieved using methods which are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HSEBP, antibodies to HSEBP, mimetics, agonists, antagonists, or inhibitors of HSEBP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HSEBP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HSEBP or fragments thereof, antibodies of HSEBP, agonists, antagonists or inhibitors of HSEBP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HSEBP may be used for the diagnosis of conditions or diseases characterized by expression of HSEBP, or in assays to monitor patients being treated with HSEBP or agonists thereof. The antibodies useful for diagnostic purposes may be prepared in the same manner as those described above for therapeutics. Diagnostic assays for HSEBP include methods which utilize the antibody and a label to detect HSEBP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HSEBP are known in the art and provide a basis for diagnosing altered or abnormal levels of HSEBP expression. Normal or standard values for HSEBP expression are established by combining body fluids or cell extracts taken from normal mammalian subjects, preferably human, with antibody to HSEBP under conditions suitable for complex formation. The amount of standard complex formation may be quantified by various methods, but preferably by photometric, means. Quantities of HSEBP expressed in subject, control and disease, samples from biopsied tissues are compared with the standard values. Deviation between standard and subject values establishes the parameters for diagnosing disease.

In another embodiment of the invention, the polynucleotides encoding HSEBP may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of HSEBP may be correlated with disease. The diagnostic assay may be used to distinguish between absence, presence, and excess expression of HSEBP, and to monitor regulation of HSEBP levels during therapeutic intervention.

In one aspect, hybridization with PCR probes which are capable of detecting polynucleotide sequences, including genomic sequences, encoding HSEBP or closely related molecules, may be used to identify nucleic acid sequences which encode HSEBP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HSEBP, alleles, or related sequences.

Probes may also be used for the detection of related sequences, and should preferably contain at least 50% of the nucleotides from any of the HSEBP encoding sequences. The hybridization probes of the subject invention may be DNA or RNA and derived from the nucleotide sequence of SEQ ID NO:2 or from genomic sequence including promoter, enhancer elements, and introns of the naturally occurring HSEBP.

Means for producing specific hybridization probes for DNAs encoding HSEBP include the cloning of nucleic acid sequences encoding HSEBP or HSEBP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HSEBP may be used for the diagnosis of conditions or diseases which are associated with expression of HSEBP. Examples of such conditions or diseases include cancers of the liver, kidney, lung, mammary, epithelial, gastrointestinal, and endocrine glands. The polynucleotide sequences encoding HSEBP may be used in Southern or northern analysis, dot blot, or other membrane-based technologies; in PCR technologies; or in dip stick, pin, ELISA or chip assays utilizing fluids or tissues from patient biopsies to detect altered HSEBP expression. Such qualitative or quantitative methods are well known in the art.

In a particular aspect, the nucleotide sequences encoding HSEBP may be useful in assays that detect activation or induction of various cancers, particularly those mentioned above. The nucleotide sequences encoding HSEBP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HSEBP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HSEBP, a normal or standard profile for expression is established. This may be accomplished by combining body fluids or cell extracts taken from normal subjects, either animal or human, with a sequence, or a fragment thereof, which encodes HSEBP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HSEBP may involve the use of PCR. Such oligomers may be chemically synthesized, generated enzymatically, or produced from a recombinant source. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HSEBP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode HSEBP may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding HSEBP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as a mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HSEBP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HSEBP and the agent being tested, may be measured.

Another technique for drug screening which may be used provides for high throughput screening of compounds having suitable binding affinity to the protein of interest as described in published PCT application WO84/03564. In this method, as applied to HSEBP large numbers of different small test compounds are synthesized on a solid substrate, such as plastic pins or some other surface. The test compounds are reacted with HSEBP, or fragments thereof, and washed. Bound HSEBP is then detected by methods well known in the art. Purified HSEBP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HSEBP specifically compete with a test compound for binding HSEBP. In this manner, the antibodies can be used to detect the presence of any peptide which shares one or more antigenic determinants with HSEBP.

In additional embodiments, the nucleotide sequences which encode HSEBP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I COLNNOT11 cDNA Library Construction

The COLNNOT11 cDNA library was constructed from normal colon tissue (on microscopic examination) obtained from a 60-year-old Caucasian male who had undergone a left hemicolectomy to remove grade 3 (of 4) adenocarcinoma in a different part of his bowel. The patient reported blood in his stool and changing bowel habits. The patient history reported previous diagnoses of depressive disorder and thrombophlebitis, accompanied by inflammatory polyarthropathies and inflammatory disease of the prostate. The patient also had undergone a vasectomy and resection of the rectum. The patient was prescribed with Seldane (terfenadin; Marion Merrell Dow Inc., Kansas City, Mo.).

The frozen tissue was homogenized and lysed using a Brinkmann Homogenizer Polytron PT-3000 (Brinkmann Instruments, Westbury, N.Y.) in guanidinium isothiocyanate solution. The lysate was centrifuged over a 5.7M CsCl cushion using an Beckman SW28 rotor in a Beckman L8–70M Ultracentrifuge (Beckman Instruments, Fullerton, Calif.) for 18 hours at 25,000 rpm at ambient temperature. The RNA was extracted with acid phenol, pH 4.0, precipitated using 0.3M sodium acetate and 2.5 volumes of ethanol, resuspended in RNase-free water and DNase treated at 37° C. The RNA extraction was repeated with acid phenol, pH 4.0, and precipitated with sodium acetate and ethanol as above. The MRNA was then isolated using the Qiagen Oligotex kit (QIAGEN Inc, Chatsworth, Calif.) and used to construct the cDNA library.

The MRNA was handled according to the recommended protocols in the SuperScript Plasmid System for cDNA Synthesis and Plasmid Cloning (Cat. #18248-013; Gibco BRL). cDNAs were fractionated on a Sepharose CL4B column (Cat. #275105-01; Pharmacia), and those cDNAs exceeding 400 bp were ligated into pSport I. The plasmid pSport I was subsequently transformed into DH5a™ competent cells (Cat. #18258-012; Gibco BRL).

II Isolation and Sequencing of cDNA Clones

Plasmid DNA was released from the cells and purified using the REAL Prep 96 Plasmid Kit (Cat. #26173; QIAGEN, Inc). This kit enables the simultaneous purification of 96 samples in a 96-well block using multi-channel reagent dispensers. The recommended protocol was employed except for the following changes: 1) the bacteria were cultured in 1 ml of sterile Terrific Broth (Cat. #22711, LIFE TECHNOLOGIES™) with carbenicillin at 25 mg/l and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger, F. and A. R. Coulson (1975; J. Mol. Biol. 94:441 f), using a Hamilton Micro Lab 2200 (Hamilton, Reno, Nev.) in combination with Peltier Thermal Cyclers (PTC200 from MJ Research, Watertown Mass.) and Applied Biosystems 377 DNA Sequencing Systems; and the reading frame was determined.

III Homology Searching of cDNA Clones and Their Deduced Proteins

Each cDNA was compared to sequences in GenBank using a search algorithm developed by Applied Biosystems and incorporated into the INHERIT™ 670 sequence analysis system. In this algorithm, Pattern Specification Language (TRW Inc., Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook, J. et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HSEBP occurs. Abundance and percent abundance are also reported. Abundance directly reflects the number of times a particular transcript is represented in a cDNA library, and percent abundance is abundance divided by the total number of sequences examined in the cDNA library.

V Extension of HSEBP-Encoding Polynucleotides to Full Length or to Recover Regulatory Sequences Full length HSEBP-encoding nucleic acid sequence (SEQ ID NO:2) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M.J. Research, Watertown, Mass.) and the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQuick™ (QIAGEN Inc.). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent *E. coli* cells (in 40 µl of appropriate media) are transformed with 3 µl of ligation mixture and cultured in 80 µl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 µl of liquid LB/2× Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer, and one or both of the gene specific primers used for the extension reaction are added to each well. Amplification is performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 µCi of [γ-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7% agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT ARTM film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

Antisense molecules to the HSEBP-encoding sequence, or any part thereof, is used to inhibit in vivo or in vitro expression of naturally occurring HSEBP. Although use of antisense oligonucleotides, comprising about 20 base-pairs, is specifically described, essentially the same procedure is used with larger cDNA fragments. An oligonucleotide based on the coding sequences of HSEBP, as shown in FIGS. 1A,B,C, is used to inhibit expression of naturally occurring HSEBP. The complementary oligonucleotide is designed from the most unique 5' sequence as shown in FIG. 1A and used either to inhibit transcription by preventing promoter binding to the upstream nontranslated sequence or translation of an HSEBP-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIG. 1A.

VIII Expression of HSEBP

Expression of HSEBP is accomplished by subcloning the cDNAs into appropriate vectors and transforming the vectors into host cells. In this case, the cloning vector, pSport, previously used for the generation of the cDNA library is used to express HSEBP in *E. coli*. Upstream of the cloning site, this vector contains a promoter for B-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HSEBP into the bacterial growth media which can be used directly in the following assay for activity.

IX Demonstration of HSEBP Activity

HSEBP can be expressed by transforming a mammalian cell line such as COS7, HeLa or CHO with an eukaryotic expression vector encoding HSEBP. Eukaryotic expression vectors are commercially available and the techniques to introduce them into cells are well known to those skilled in the art. The cells are incubated for 48–72 hours after transformation under conditions appropriate for the cell line to allow expression and accumulation of HSEBP.

A small amount of radioactive [$^{75}$Se]-selenite is added to the culture media 12–24 hours prior to harvesting the cells. The cells are washed in cold buffer to remove excess selenite, lysed with detergent, and the solubilized proteins resolved by SDS-polyacrylamide gel electrophoresis; marker proteins of known molecular weight (BioRad, Hercules, Calif.) can be electrophoresed in parallel lanes of the gel and used to calibrate sizes. Following electrophoresis, the gel is exposed against Kodak X-OMAT AR film (Kodak, Rochester, N.Y.) for a suitable period of time. A band will be visible on the film at the position expected for a protein of the predicted size for HSEBP. A comparison can be made with the Se-binding proteins present in untransformed cells or with cells transformed with vector sequences alone.

X Production of HSEBP Specific Antibodies

HSEBP that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431 A using finoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HSEBP Using Specific Antibodies

Naturally occurring or recombinant HSEBP is substantially purified by immunoaffinity chromatography using antibodies specific for HSEBP. An immunoaffinity column is constructed by covalently coupling HSEBP antibody to an activated chromatographic resin, such as CnBr-activated Sepharose (Pharmacia & Upjohn). After the coupling, the resin is blocked and washed according to the manufacturer's instructions.

Media containing HSEBP is passed over the immunoaffinity column, and the column is washed under conditions that allow the preferential absorbance of HSEBP (e.g., high ionic strength buffers in the presence of detergent). The column is eluted under conditions that disrupt antibody/HSEBP binding (e.g., a buffer of pH 2–3 or a high concentration of a chaotrope, such as urea or thiocyanate ion), and HSEBP is collected.

XII Identification of Molecules Which Interact with HSEBP

HSEBP or biologically active fragments thereof are labeled with [$^{125}$I]-Bolton-Hunter reagent (Bolton et al. (1973) Biochem. J. 133:529). Candidate molecules previously arrayed in the wells of a multi-well plate are incubated with the labeled HSEBP, washed and any wells with labeled HSEBP complex are assayed. Data obtained using different concentrations of HSEBP are used to calculate values for the number, affinity, and association of HSEBP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding the HSEBP (human selenium binding protein), having the amino acid sequence represented by SEQ. ID. NO:1.

2. A polynucleotide sequence which hybridizes under stringent conditions to the polynucleotide sequence of claim 1.

3. A hybridization probe having the polynucleotide sequence of claim 1.

4. An isolated and purified polynucleotide sequence represented by SEQ ID NO:2.

5. A polynucleotide sequence which is complementary to SEQ ID NO:2.

6. A hybridization probe having the polynucleotide sequence of claim 5.

7. An expression vector containing the polynucleotide sequence of claim 1.

8. A host cell containing the vector of claim 7.

9. A method for producing a polypeptide having the amino acid sequence of claim 1, the method comprising the steps of:

a) culturing the host cell of claim 8 under conditions suitable for the expression of the polypeptide; and
   b) recovering the polypeptide from the host cell culture.

* * * * *